United States Patent [19]
Genevier et al.

[11] Patent Number: 5,361,759
[45] Date of Patent: Nov. 8, 1994

[54] MECONIUM MONITORING SYSTEM

[75] Inventors: Eric S. G. Genevier, London; Philip J. Steer, Kingdyon upon Thames; Peter J. Danielian, Aberdeen; Nigel J. Randall, London; Robin W. Smith, Crovdon, all of England

[73] Assignee: Charing Cross & Westminster Medical School, London, England

[21] Appl. No.: 84,465

[22] Filed: Jul. 1, 1993

Related U.S. Application Data

[63] Continuation-in-part of Ser. No. 978,710, Feb. 1, 1993, abandoned.

[30] Foreign Application Priority Data

Jul. 4, 1990 [GB] United Kingdom ............... 9014786.9
Jul. 1, 1992 [GB] United Kingdom ............... 9213987.2

[51] Int. Cl.$^5$ ................................................ A61B 6/00
[52] U.S. Cl. ...................................... 128/634; 128/665
[58] Field of Search ........................... 128/633.4, 664.5; 356/39–41

[56] References Cited

U.S. PATENT DOCUMENTS

| | | | |
|---|---|---|---|
| 4,856,527 | 8/1989 | Karcher et al. | 128/634 |
| 4,938,218 | 7/1990 | Goodman et al. | 128/633 |
| 5,024,226 | 1/1991 | Tan | 128/633 |
| 5,048,524 | 9/1991 | Bailey | 128/634 |
| 5,172,693 | 12/1992 | Doody | 128/633 |

Primary Examiner—Angela D. Sykes
Attorney, Agent, or Firm—Sughrue, Mion, Zinn, Macpeak and Seas

[57] ABSTRACT

A system for in vivo monitoring of the presence and concentration of meconium and/or blood in amniotic fluid during labor by spectral analysis includes a probe for insertion in the uterus, the probe having a flexible body housing an optical cell. The probe has at least one aperture so that amniotic fluid can enter the cell. A fiber optic cable connects the cell to a light source and to a spectral analyzer, and the probe includes structure for shielding the fiber optic cable from any light scattered by the wall of the uterus or fetus.

14 Claims, 5 Drawing Sheets

Blood stained amniotic fluid spectrum with expected baseline.

MECONIUM MONITORING SYSTEM

This is a continuation-in-part of U.S. application Ser. No. 07/978,710 filed Feb. 1, 1993, now abandoned.

BACKGROUND OF THE INVENTION

This application relates to a system and method for monitoring the quality of amniotic fluid during labor.

In recent years, it has become accepted that there is a need for more information concerning the condition within the uterus just prior to and during labour in order to predict and avoid birth complications. U.K. Patent Application No. 87 23605 (Publication No. 2195897) describes an intrauterine probe which enables certain conditions, especially the fetal heart rate and the intrauterine pressure to be continuously monitored during labor. Any monitoring system should desirably be non-invasive to the fetus and be capable of a continuous collection of data concerning the condition of interest.

During intrauterine life, the human fetus collects within its bowel a collection of debris known as meconium. Passage of meconium in utero occurs in about 10% of babies overall, probably as part of a sympathetic 'fright, flight or fight' reaction. Because regular uterine contractions interfere with maternal blood flow within the placenta, the mean oxygen tension in fetal blood during labour drops from about 5 to 3 kPa. This is thought to be the major stimulus causing the fetus to pass meconium in utero; it occurs with increasing frequency as gestation advances, reaching almost one third of all fetuses by 42 weeks gestation.

In 90% of fetuses who pass meconium into the amniotic fluid there are no harmful effects. However, in about 10% of cases the fetus gasps, inhaling the sticky, particulate meconium into the upper respiratory tract. Once the baby is born, this particulate matter produces partial airways obstruction, leading to inability to inflate alveoli in some areas, and hyperinflation in others. This disease is known as meconium aspiration syndrome (MAS).

Attempts have been made to prevent MAS by careful suctioning of the baby's pharynx immediately after the head is delivered; unfortunately such measures are largely ineffective.

It appears that there is, as yet, no known effective prevention of this crippling and disabling condition. The main factor preventing progress is that the appearance of meconium into the amniotic fluid often remains undetected because the tight fit of the head in the pelvis does not allow amniotic fluid to drain out and become visible to the attending obstetrician.

There is therefore a need for a method of reliably monitoring the onset of meconium passage into the amniotic fluid and particularly one which can be carried out non-invasively to the fetus and continuously throughout labor.

SUMMARY OF THE INVENTION

According to one aspect of the present invention, there is provided a non-invasive system for monitoring the content of amniotic fluid during labour which comprises an optical cell supported in a probe capable of insertion into the uterus during labour, said cell being connected optically to a source of light (having a suitable spectral bandwidth) and to photodetecting means for detecting the spectral response of the amniotic fluid to illumination with said source and processing means for determining the presence of meconium and/or blood in the amniotic fluid by analysis of the spectral response.

According to a second aspect of the present invention there is provided an intrauterine probe which comprises a flexible elongated body and an optical cell housed therein, the cell being optically connected by fibre optic cables to the distal end and the cell being located in the housing in such a way that in use amniotic fluid is able to pass through the cell.

The inventors experience with the probe has demonstrated the importance of excluding any light which is scattered by the uterine wall or the skin of the fetus. Such randomly scattered light tends to give a spurious signal indicative of the presence of blood, because the uterine wall is richly supplied with blood vessels.

According to a further aspect of the present invention therefore there is provided an intrauterine probe which comprises a flexible body housing an optical cell, said cell including at least one aperture permitting entry of amniotic fluid and being connected at one end to a fibre optic cable for conducting light reflected from the amniotic fluid to spectral analysis means, said cell also having shielding means to shield the fibre optic cable from any light scattered by the wall of the uterus or the fetus.

Preferably, the probe has a flattened form and is designed so that the generally flat faces of the probe contact the fetus on one side and the wall of the uterus on the other. With such a design, the entry to the optical cell for amniotic fluid is via the sides which are generally at right angles to the flattened faces of the probe and the optical cell within the probe is shielded by flattened portions of the sides of the probe. It is also preferred that the optical cell has at least two apertures so that amniotic fluid can flow freely through the optical cell.

BRIEF DESCRIPTION OF THE DRAWING

Further features and advantages of the present invention will become apparent from the following detailed description and accompanying drawings in which.

DETAILED DESCRIPTION OF THE PREFERRED EMBODIMENTS

Figure 1:
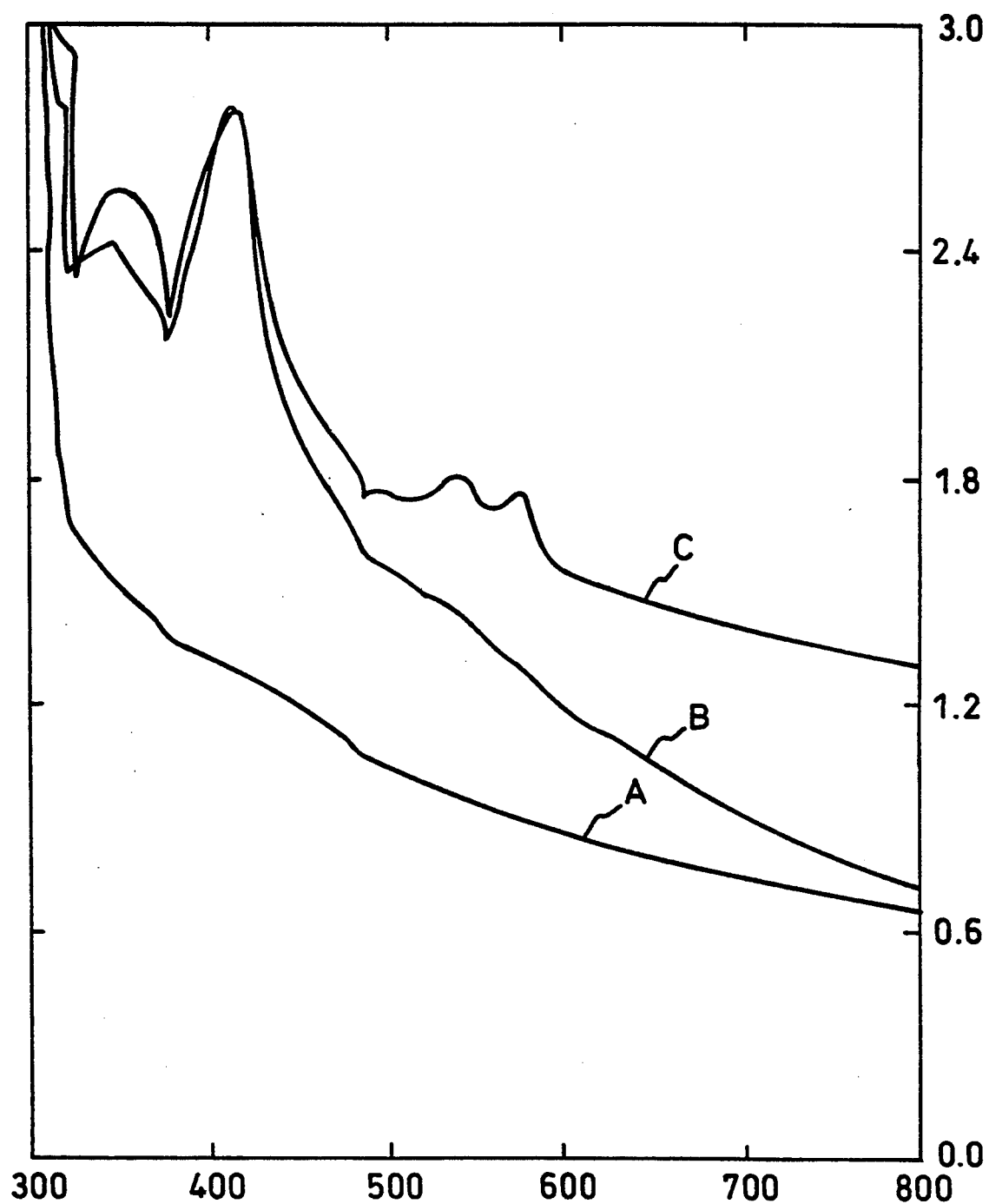
FIG. 1 is an absorption spectrum of three samples A, B & C of different amniotic fluids.

Two difficulties in making direct observations of the absorption spectrum of amniotic fluid are first to differentiate the spectra for meconium and blood, and secondly, to take into account the differing overall opacities between different samples of amniotic fluid. Typical spectra are shown in FIG. 1, where A is the spectrum of a sample clear of meconium and blood, whereas B is the spectrum of a meconium stained sample showing a strong absorption peak in the range of 405 to 415 nm, and C that of a blood stained sample. It can be seen that spectrum C has a major peak in the range of 405 to 415 nm and two minor peaks in the range 535 to 545 nm and 570 to 580 nm.

The effect of blood on the absorption spectrum is important as it affects the whole spectrum in the range 405 to 415 nm, where it adds a wide band peak in the same way as meconium does, the main difference between the two spectra being the two peaks seen at 540 and 575 nm, and the fact that meconium absorbs poorly above about 650 nm.

In order to account for the different opacities and distinguish between clear, meconium or blood-stained amniotic fluid, the system and method of the present invention involves a comparison of the spectral response at different wavelengths. One way in which this can be done is to measure the absorption spectrum of the amniotic fluid in the areas corresponding to the peaks produced by meconium and blood and at a third wavelength which is distant from the peaks characteristic of meconium and blood. In this way a base line value can be subtracted from the peak absorption values of the fluid under test. This procedure is illustrated graphically in FIG. 2 which is a spectrum of a blood-stained sample of amniotic fluid containing meconium. It will be seen from FIG. 2 that the point at 500 nm can be taken as the base line. From these three absorption values we can derive the following variables:

$$\delta(405) = K1 \cdot [A(405) - A(500)]$$

$$\delta(575) = K2 \cdot [A(500) - A(575)]$$

where:
A(405)=absorption at 405 nm
A(500)=absorption at 500 nm
A(575)=absorption at 575 nm These variables are referred to hereinafter as the compensated absorption values. K1 and K2 are arbitrary constants to bring both values in the range 0 to 1.

For a sample clear of meconium and blood, $\delta(405)$ and $\delta(575)$ are both positive. As the level of meconium is increased, both $\delta(405)$ and $\delta(575)$ should increase but in the case where blood is also present, $\delta(575)$ does not increase significantly and often decreases to become negative, this is because the addition to the spectrum of a peak at 575 nm reduces the difference A(500)–A(575).

Therefore, should blood appear in the amniotic fluid when meconium is already present, blood would immediately be detected, which is important as the appearance of blood in the amniotic fluid is a life-threatening condition requiring immediate attention.

While absorption measurements can be used to discriminate amniotic fluid containing meconium or blood and clear fluid, a perfectly normal amniotic fluid may be extremely turbid because of the presence of vernix (a waxy substance which covers the fetus). In such circumstances, the vernix contamination makes it difficult to obtain meaningful absorption measurements, except possibly in very thin films or after removal of a sample and centrifugation to clear the sample. The latter procedure is not usually possible where continuous monitoring is required.

A preferred procedure for analysing the spectral response of the amniotic fluid to illumination involves measurement of back scattered light (i.e. reflected) from a sample of the fluid. An amniotic fluid which is contaminated with vernix has a milky appearance and reflects light strongly over a wide waveband. As meconium increases in the amniotic fluid, it is also responsible for scattering light. Further, increased turbidity of the fluid will result in a reflected signal of increased strength.

Figure 2:
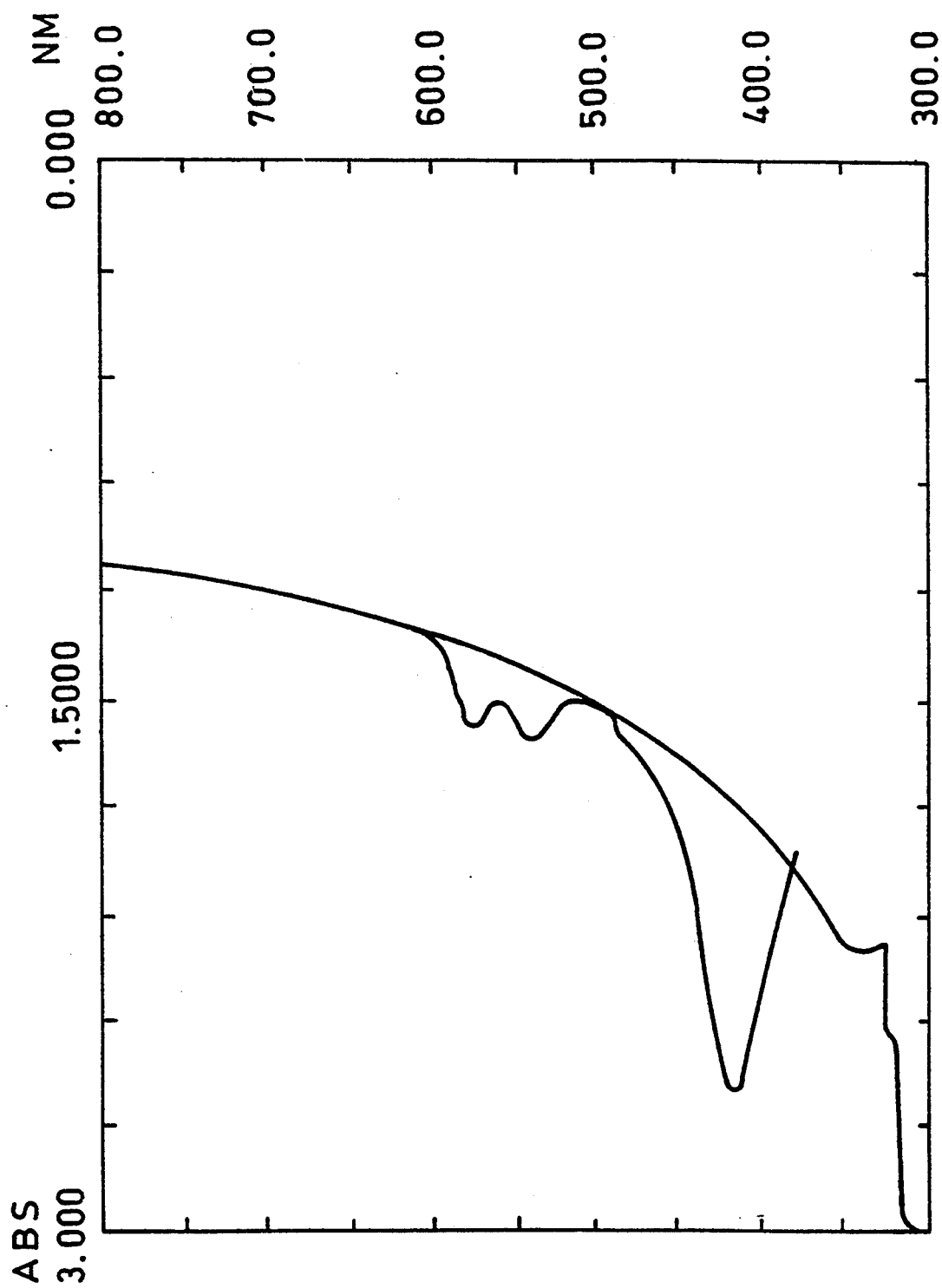
FIG. 2 is an absorption spectrum of a blood-stained sample of amniotic fluid with expected base line.

It is, however, possible to distinguish increases in reflectance due to the presence of maconium, as opposed to vernix or other contaminants, by exploiting the optical absorption characteristics of meconium as mentioned above. Because meconium absorbs light in the range of about 402 to 420 nm, measurement of reflected values in this waveband compared with reflectance values at a wavelength where there is no significant absorption by meconium makes it possible to estimate the concentration of meconium. Observations have shown that light reflected from a sample of the fluid at 405 to 420 nm increases with meconium concentration until a certain point (which is not necessarily the same from one sample to the next), where it starts to decrease due to the absorbing properties of meconium in that range. In contrast, reflectance values at, for example, 700 nm continue to increase up to the maximum concentration measured (100 g of meconium per liter). Blood can be differentiated in a similar way by measuring the reflectance at a third wavelength where blood absorbs light but meconium does not (540 nm has been found to be suitable) and also at 700 nm, where like meconium its absorption is small. Although FIG. 1 may suggest at first sight that light absorption by blood at 700 nm is significant, the spectrum at 700 nm is, in fact, the overall attenuation of a light beam due to both absorption and scattering of light. According to the Beer Lambert Law, the intensity I of a monochromatic light beam of initial intensity $I_o$ passing through a medium of path length d and concentration c is:

$$I = I_o e^{-ad}$$

where a is the attenuation coefficient which is plotted in FIGS. 1 and 2. The attenuation coefficient is, in fact, the sum of the absorption and scattering coefficients and is related to concentration of the substance under investigation in the following way:

$$a = (a_1 + a_2)c$$

where $a_1$ is the absorption coefficient and $a_2$ is the scattering coefficient.

The scattering coefficient for blood is much larger than for meconium, but the absorption coefficients of both meconium and blood are insignificant at 700 nm and can be ignored. Therefore, 700 nm provides a suitable base line for concentration determinations when using reflectance measurements for both blood and meconium by logarithmic treatment of the reflectance measurements at 405 to 420 nm, 540 nm and 700 nm. Thus, by measuring the intensity of the illuminating light (and its spectral content), the intensity of incident light at each wavelength of interest (e.g. 405–420, 540 & 700 nm) can be calculated. Using these values and the values of reflected light at the same three wavelength, the reflection due to the vernix content can be allowed for and compensated reflectance values calculated which are related to the content of meconium and blood in the amniotic fluid. From these compensated values, the concentration of meconium and blood can be calculated with a reasonable degree of accuracy.

Figure 3:
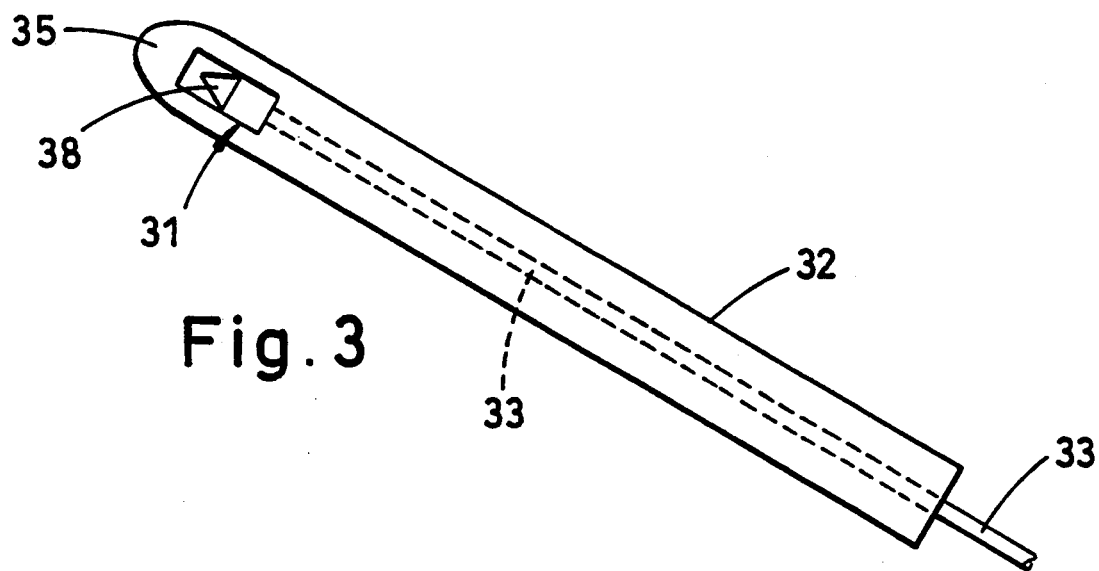
FIG. 3 is a perspective diagrammatic view of an intrauterine probe in accordance with the invention.

Optical measurements can be conveniently made in vivo, using a flexible intrauterine probe of the kind described in British patent application No. 8723605 (Publication No. 2195897). This is illustrated diagrammatically in FIG. 3. As described in our above application, the probe is moulded from a suitable plastics material such as polyurethane and is stiff and resilient enough to enable it to be inserted by pushing into the uterus from the proximate end through the cervix and around the fetal head. The shape and dimensions and mechanical properties of the body of the probe are preferably as described in UK Patent Specification No. 2,195,897, the disclosure of which is incorporated herein. Optical measurements are made using an optical cell which is encapsulated in a potting composition from which the probe is formed. The optical cell is preferably constructed in such a way that fluid can flow from one side of the probe through to the other by passing through passages in the cell. Thus referring to FIG. 3, the optical cell 31 is encapsulated in the body 32 of the probe and the cell is optically connected to an optic fibre bundle 33, also encapsulated in the body 32. Bundle 33 emerges from the proximate end of the probe from which it is optically connected (indicated diagrammatically in FIG. 5) to photodetectors.

Figure 4:
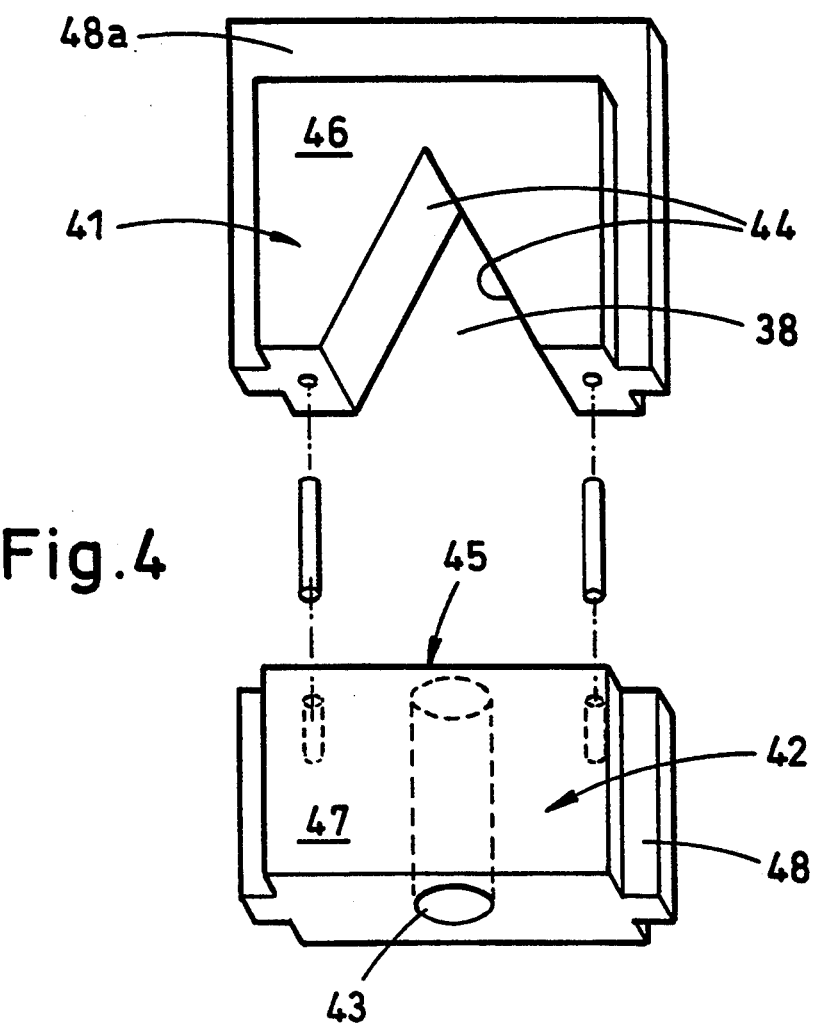
FIG. 4 is an exploded view of an optical cell on an enlarged scale.

The cell is shown in FIG. 4 and is manufactured in two inter-engaging parts (41 & 42). FIG. 4 shows the cell in an exploded view. Part 42 includes a bore 43 (typically about 3 mms in diameter), for receiving the fibre optic bundle 33 (not shown in FIG. 4). The fibre optic bundle comprises a large number of optic fibres which are located in bore 43 and preferably sealed in place with a suitable thermoplastic resin, e.g. an epoxy resin to prevent ingress of amniotic fluid by capillary action. Suitable optic fibre bundles are supplied by Fibre Data Limited, Unit 8, Pool Industrial Estate, Druids Road, Redruth, Cornwall TR15 3RH. The particular fibre bundle employed contained about 540 silica fibres and was randomly divided into two equal branches (known as a 'Y' shape bifurcated bundle), one branch serves to transmit light into the optical cell and the other collects the reflected light and conveys it to the spectrophotometer, comprising the photodetectors. When assembled, part 42 is secured to part 41 by the screws or studs indicated. Part 41 is shaped to provide conical or triangular-shaped counter-surfaces which prevent light which strikes such surfaces from being reflected back into the optic fibre-ends 45 of bore 43. Preferably, the internal faces 44 are coated with an anti-reflecting material or are roughened to minimise reflection.

When encapsulated in the material forming the body of the probe, faces 46 & 47 of parts 41 & 42 will be parallel with the flat surfaces 35 of the probe and flanges 48 & 48A of parts 41 & 42 will serve to lock the parts into the body of the probe. However, a passage 38 remains open through the probe and cell so that in use amniotic fluid may pass through the cell from one side of the probe to the other. Because the flat face 35 of the probe will in use lie against the wall of the uterus, light cannot be reflected from the uterus into the optic fibre bundle which is important since the wall of the uterus is red and would give a spurious signal.

Figure 5:
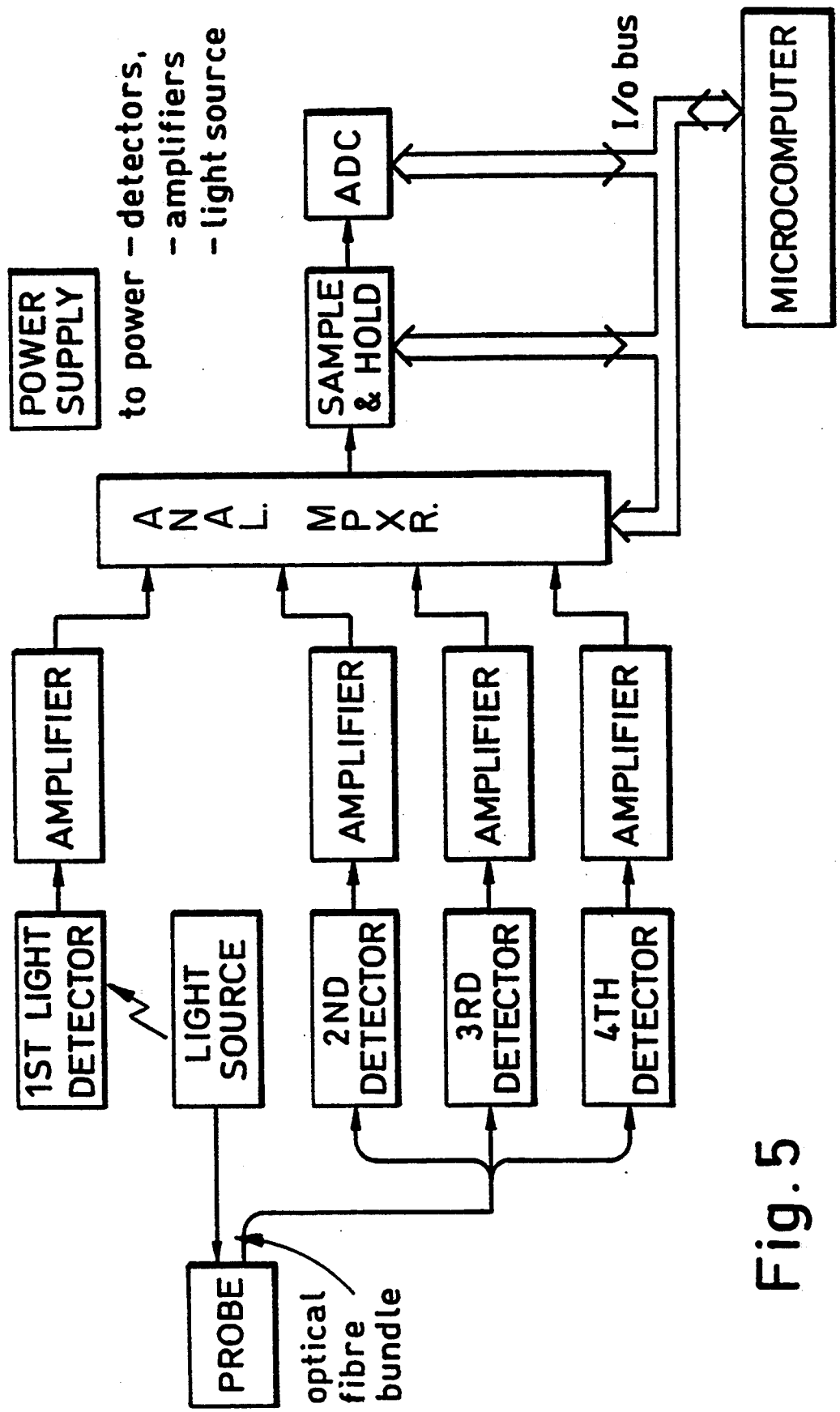
FIG. 5 is a block diagram illustrating the signal processing equipment.

FIG. 5 shows a block diagram of the processing system. As illustrated in the block diagram, light from the source is fed to the probe via the optic fibre bundle and a first light detector is linked to the light source and measures its intensity. Reflected light is returned from the probe to second, third and fourth photodetectors (which may be photodiodes) and are tuned to detect the reflectance values at the three wavelengths of interest, i.e. 405-420 nm, 540 nm, and 700 nm, respectively. After amplification, the signals are fed via an analogue multiplexer and an analogue-digital converter to a microcomputer.

The light source used to illuminate the sample passing the optical cell may be any suitable light source of sufficient intensity at the three desired wavelengths.

Preferably, the light source is a tungsten halogen filament bulb, although any light source emitting light at 415, 540 and 700 nm would be suitable. The tungsten halogen lamp has the advantage that, while the total intensity fluctuates with temperature, the spectral content remains constant. Thus, by measuring overall intensity, the intensity delivered at each of the three selected wavelengths can easily be calculated.

The optical components and electronics circuitry can be housed together in a box adjacent to the bed and linked to probe. The output from this box may be taken to a central processing unit such as a microcomputer via a suitable interface. This arrangement enables the compensated reflectances to be calculated automatically and in real time, logged and displayed on a VDU or any suitable display in terms of corresponding concentrations of meconium and blood, or a hard copy record to be produced. Alternatively, a simpler read-out can be employed which merely gives an indication, when meconium and/or blood is detected at a level which suggests cause for alarm.

Figure 6:
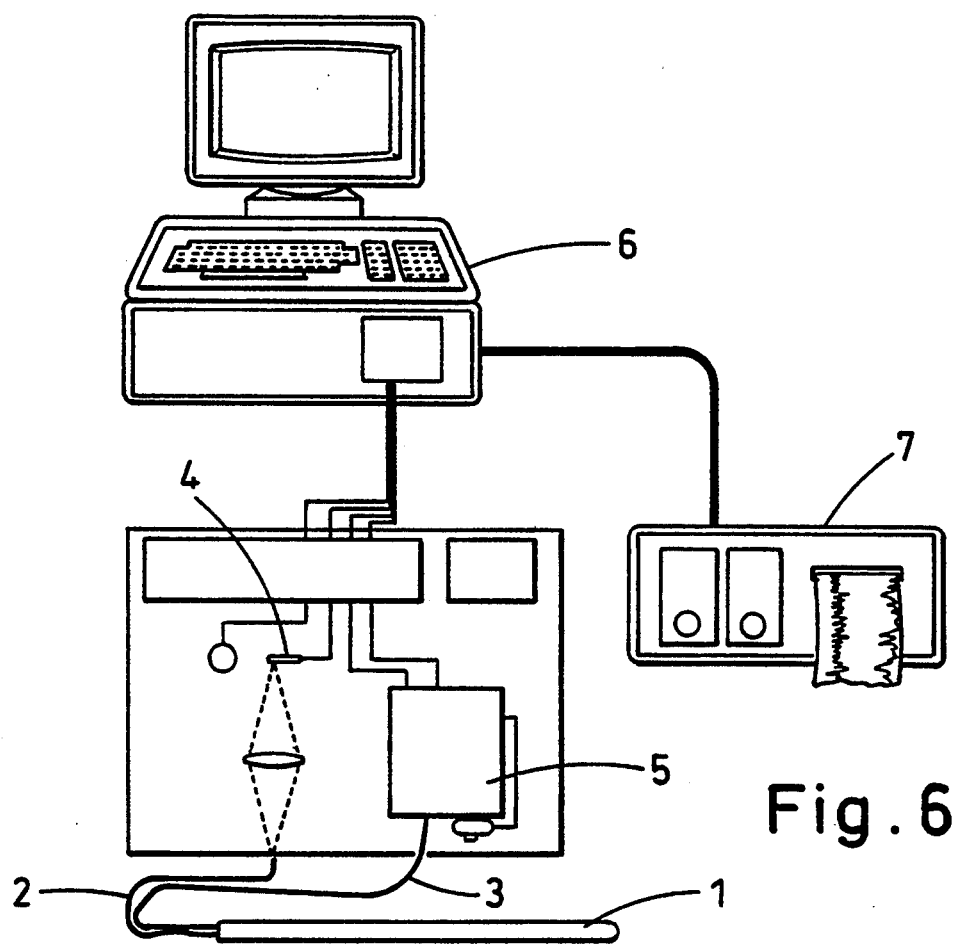
FIG. 6 is a general arrangement showing the layout of a modified system in accordance with the invention.

Referring to FIG. 6, the system layout is similar to that described in the earlier Figures and incorporates a flexible probe 1 which is linked by fibre optic cables 2 and 3 respectively to a broad spectrum light source such as a tungsten halogen lamp or a xenon arc lamp. A xenon arc lamp is preferred since it is rich in radiation around the 405-415 nm band which includes the meconium absorption peak.

Fibre optic cable 3 is connected to spectral analysis equipment 5 for measuring back scattered light from the amniotic fluid. A typical system is the Monolight Optical Spectrum Analyser System 6800, manufactured by Monolight Limited of Weybridge, Surrey. This system consists of a diffraction grating with an input slit width of 0.89 mms achieving a band width resolution of 10 nm and has a photomultiplier tube with a variable output gain and a 12 bit analogue to digital converter. The converter is connected to an IBM PC and the results displayed on the screen. The spectra of the back scattered light were measured in the range of 300 to 900 nm. The probe may also include a pressure sensor and/or electrodes, e.g. as described in UK Patents Nos. 2195897 and 2216904 and EP No. 0325605, (the disclosure of which is specifically incorporated herein) and the data collected, i.e. fetal heart rate and intrauterine pressure displayed on the screen or on a separate monitor 7.

Figure 7A:
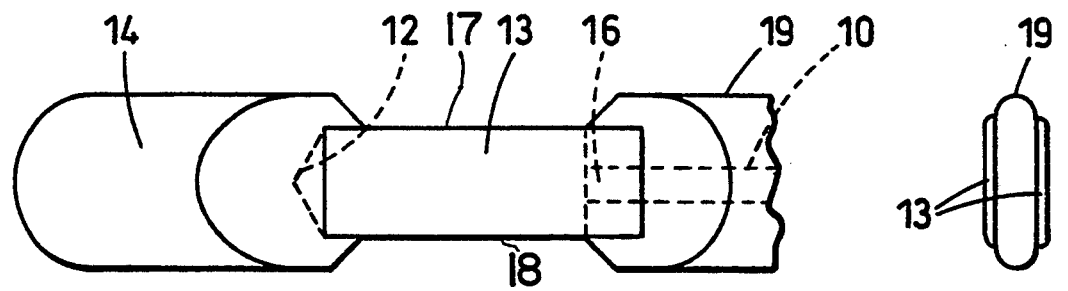
FIG. 7A is a side elevation of the tip of another embodiment of a probe.
Figure 7B:
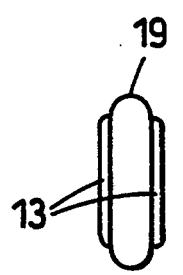
FIG. 7B is an end view of the tip of the probe shown in FIG. 6.
Figure 7C:
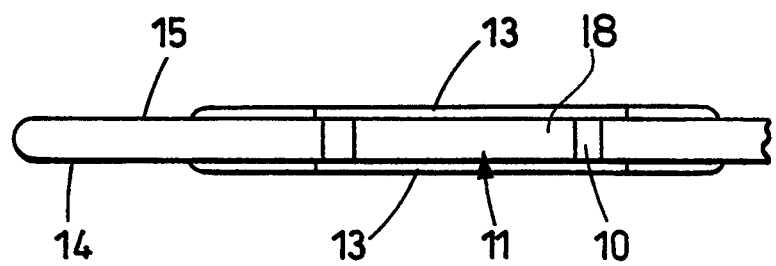
FIG. 7C is a view of the tip of the probe seen in the direction of the arrow A in FIG. 7A.

Referring to FIGS. 7A, 7B and 7C, the fibre optic cables 2 and 3 were merged together in the body of the probe 1 to form a merged bundle 10 which terminated at one end of the optical cell 11. The other end 12 of the optical cell opposite to the ends of the fibre optic cable constitutes a "beam dump" and forms a cavity having sides forming an approximate right angle. This shape and the black colouration of the probe body ensures that light striking end 12 of the cell, e.g. light entering from the transmission part of the fibre optic bundle is efficiently absorbed and not reflected back into the receptor fibres of the cable.

As shown, the sides of the optical cell comprise a pair of strip-like shielding members 13 which ensure that any light reflected from the uterine wall against which the face 14 or 15 may be pressed is not reflected into the end of the fibre optic bundle 16. In the embodiment illustrated the members 13 are formed separately from the body of the probe and are bonded to the distal end and the main body of the probe to form the optical cell. Alternatively, of course, the parts 13 may be constructed integrally with the body of the probe (e.g. as a moulding or extrusion). It is, however, thought to be advantageous that the entry to the apertures 17 and 18 are recessed from the general upper surface 19 of the probe body. It is believed that in the uterus during labour the amniotic fluid may be trapped in pools between portions of the uterine wall and the fetus and the design shown in FIGS. 7A through 7C tends to encourage amniotic fluid to flow along the surfaces 19 of the probe and into the optical cell.

Half the fibres in the silica optic fibre bundle of approximately 1000 fibres were randomly chosen for transmitting light and the others to receive light back scattered from the amniotic fluid. The fibre bundle was encapsulated in the body of the intrauterine probe with its tip 16 emerging at one end of the optical cell 11, approximately 50 mms from the tip of the probe.

The thickness of the probe body was approximately 4 mms and was made from polyurethane with a total length of about 400 mms and a width of about 14 mms.

The thickness of the shielding parts 13 was about 1 mm and in the design shown in the attached drawings was formed from hard PVC so as to be stiff and not to allow significant distortion of the cell during use. The cell itself was approximately 1 cm long.

We claim:

1. A non-invasive system for monitoring the content of amniotic fluid during labor comprising:
   a) an optical cell supported in a probe which is capable of insertion into the uterus during labor, said cell having a passageway permitting flow of amniotic fluid therethrough,
   b) a source of light of suitable spectral bandwidth optically connected to the cell,
   c) photodetecting means optically connected to the cell for detecting light reflected from the amniotic fluid, and
   d) processing means for determining the presence of meconium and/or blood in the amniotic fluid by analysis of the spectral content of said reflected light,
   said cell being oriented in the probe in such a way that amniotic fluid in said passageway is illuminated by said light source while avoiding any light reflected from the wall of the uterus reaching the photodetecting means.

2. A system according to claim 1 in which the light source and the photodetecting means are located remotely from the probe and are connected to the cell by fiber optic cable.

3. A system according to claim 2 in which the fiber optic cable comprises a bundle of fibers, some of said fibers being optically connected with the light source and others with the photodetecting means.

4. A system according to claim 1 in which the photodetecting means includes first and second photodetectors tuned to detect light reflected at first and second wavelengths at which meconium and blood, respectively, strongly absorb light and a third detector tuned to detect light at a third wavelength at which meconium and blood do not absorb light significantly.

5. A system according to claim 4 in which the first wavelength is about 405 to 420 nm, the second wavelength is about 540 nm and the third wavelength is about 700 nm.

6. An intrauterine probe according to claim 1 wherein the probe comprises a flexible elongated body having a proximal and a distal end and an optical cell housed therein at said distal end, the cell being optically connected by fiber optic cable and the cell being located in the housing so that in use amniotic fluid is able to pass through said passageway in the cell.

7. A probe according to claim 6 wherein the cell has an interior surface which is non-reflecting.

8. A probe according to claim 6 in which the fiber optic cable comprises a bundle of fibers, some of the fibers serving to transmit light and others to convey light reflected by the amniotic fluid to the photodetecting means for detection thereat.

9. An intrauterine probe which comprises a flexible body of generally flat form having substantially flat major surfaces, said probe housing an optical cell which includes at least two apertures permitting the entry and exit of amniotic fluid (AF), said cell being connected to a fiber optic cable, for conducting light to said cell and for conducting light reflected from the AF to spectral analysis means, said probe having shielding means to shield the fiber optic cable from any light scattered by the wall of the uterus or the fetus wherein in use one of the major surfaces of the probe contacts the wall of the uterus.

10. A probe according to claim 9 in which the shielding means are generally planar with the major surfaces of the probe.

11. A probe according to claim 9 in which the substantially flat major surfaces of the probe include one or more longitudinal ribs.

12. A probe according to claim 9 in which each aperture opens into a minor surface of the probe transversely of said major surfaces.

13. A probe according to claim 9 wherein said fiber optic cable passes longitudinally through the probe body and has a tip which emerges at said cell at a first end thereof.

14. A probe according to claim 13 wherein said cell has a second end opposite said first end which is shaped such that light striking said second end is not reflected onto the tip of the fiber optic cable.

* * * * *